(12) United States Patent
Lam et al.

(10) Patent No.: US 8,166,823 B2
(45) Date of Patent: May 1, 2012

(54) MEMBRANE-COUPLED ULTRASONIC PROBE SYSTEM FOR DETECTING FLAWS IN A TUBULAR

(75) Inventors: Clive C. Lam, Tomball, TX (US);
Yanming Guo, Missouri City, TX (US);
Kevin D. Logan, Humble, TX (US);
Qingshan Yuan, Houston, TX (US)

(73) Assignee: National Oilwell Varco, L.P., Houston, TX (US)

( * ) Notice: Subject to any disclaimer, the term of this patent is extended or adjusted under 35 U.S.C. 154(b) by 66 days.

(21) Appl. No.: 12/795,833

(22) Filed: Jun. 8, 2010

(65) Prior Publication Data
US 2011/0072905 A1 Mar. 31, 2011

Related U.S. Application Data

(63) Continuation-in-part of application No. 12/568,737, filed on Sep. 29, 2009.

(51) Int. Cl.
*G01N 29/04* (2006.01)
(52) U.S. Cl. ............... 73/622; 73/600; 73/602; 73/644
(58) Field of Classification Search .............. 73/622, 73/599, 600, 602, 618, 625, 644
See application file for complete search history.

(56) References Cited

U.S. PATENT DOCUMENTS

| | | | |
|---|---|---|---|
| 4,852,416 A | 8/1989 | Boone et al. | |
| 5,254,944 A * | 10/1993 | Holmes et al. | 324/220 |
| 5,303,210 A * | 4/1994 | Bernstein | 367/181 |
| 5,585,565 A | 12/1996 | Glascock | |
| 6,578,424 B1 | 6/2003 | Ziola et al. | |
| 6,813,950 B2 * | 11/2004 | Glascock et al. | 73/633 |
| 7,270,021 B2 * | 9/2007 | Shimamura et al. | 73/865.8 |
| 7,412,890 B1 * | 8/2008 | Johnson et al. | 73/618 |
| 7,578,166 B2 | 8/2009 | Ethridge et al. | 73/1.82 |
| 7,694,509 B2 * | 4/2010 | Noirot et al. | 60/295 |
| 7,694,569 B2 | 4/2010 | McGrath et al. | |
| 7,874,212 B2 * | 1/2011 | Yamano | 73/622 |
| 2007/0175282 A1 | 8/2007 | Fetzer et al. | |
| 2008/0236286 A1 | 10/2008 | Lam et al. | |

(Continued)

FOREIGN PATENT DOCUMENTS

EP 0633451 A2 1/1995

(Continued)

OTHER PUBLICATIONS

International Search Report dated Jun. 22, 2011 of counterpart PCT Application No. PCT/US2010/048749, 7 pages.

(Continued)

*Primary Examiner* — J M Saint Surin
(74) *Attorney, Agent, or Firm* — Jeffery Daly; JL Salazar Law Firm

(57) ABSTRACT

An ultrasonic probe apparatus for detecting flaws in a tubular includes a probe housing. The probe housing has an axial axis, a central cavity lying along the axial axis, and a bottom face adapted for placement on the tubular. The bottom face of the probe housing has an opening in the middle. A probe support is disposed within the central cavity and rotatable about the axial axis of the probe housing. An ultrasonic probe is mounted on the probe support and has a scanning face exposed to the opening of the bottom face of the probe housing, and may be coupled to the pipe with a liquid acoustic couplant medium.

19 Claims, 10 Drawing Sheets

U.S. PATENT DOCUMENTS

| | | |
|---|---|---|
| 2009/0165563 A1 | 7/2009 | McGrath et al. |
| 2009/0178465 A1 | 7/2009 | Ethridge et al. ............... 73/1.82 |
| 2009/0217763 A1* | 9/2009 | Yamano .......................... 73/622 |
| 2010/0005846 A1* | 1/2010 | Yamano ....................... 72/31.13 |

FOREIGN PATENT DOCUMENTS

| | | |
|---|---|---|
| EP | 1 918 700 A1 | 5/2008 |
| JP | 2008256624 | 10/2008 |
| WO | 2008/043888 A1 | 4/2008 |

OTHER PUBLICATIONS

GE Catalog, Phased Array Probes: Ultrasonic Probes, Copyrighted 2006, printed from the internet Nov. 17, 2011, URL: http://www.holger.no/assets/pdf/Phased-array%20Iydhoder.pdf, 4 pages.

* cited by examiner

MEMBRANE-COUPLED ULTRASONIC PROBE SYSTEM FOR DETECTING FLAWS IN A TUBULAR

CROSS-REFERENCE TO RELATED APPLICATIONS

This application claims priority from, and is a continuation-in-part of presently pending U.S. patent application Ser. No. 12/568,737, filed on 29 Sep. 2009, which is incorporated by reference herein for all it contains.

BACKGROUND OF THE INVENTION

1. Field of the Invention

The present disclosure relates generally to an ultrasonic probe apparatus, an ultrasonic probe system, and an ultrasonic probe method for detecting the presence of structural and material flaws in a tubular. In particular, the disclosure relates to an ultrasonic probe apparatus which employs a single, handheld scanner and a single ultrasonic phased array probe to detect structural and material flaws, i.e. wall reduction, cracks or manufacturing defects, etc., which may occur to a tubular being manufactured or after being in operation. In particular, the probe apparatus is designed and operated in a manner to specifically determine the thickness of a wall and unacceptable defects in a pipe.

2. Description of the Related Art

Non-destructive ultrasonic test methods are commonly used in the inspection of tubulars for structural and material flaws, e.g., cracks in the tubular walls, unevenness in the thickness of the tubular walls, and delaminations and inclusions in the tubular walls. Single-element and multi-element ultrasonic probes have been used in the tests. The probes are physically oriented in different directions to detect flaws with different orientations, such as longitudinally-oriented flaws, transversely-oriented flaws, and obliquely-oriented flaws. Detection in multiple orientations using a single ultrasonic probe requires mechanical adjustment of the tilt angle of the probe for each different orientation, which is costly and time-consuming. Recently, ultrasonic phased array technology was introduced allowing flaw detection in multiple orientations. Since the ultrasonic beams from a phased array probe can be steered/tilted electronically rather than mechanically, this enables one using the phased array technology to detect flaws with various orientations in a much more efficient way. Moreover, in view of the fact that the multiple elements in a phased array are divided into different groups that can be activated in sequence to inspect different locations on the test piece, a phased array probe is capable of scanning a large inspection area without movement.

European Patent Publication No. EP 1918700 A1 discloses a method for detecting flaws in tubulars using a phased array probe. The method includes arranging the phased array probe to face a tubular test object. Selected transducers in the probe transmit and receive ultrasonic waves such that ultrasonic waves are transmitted in the tubular in a plurality of different propagation directions. Transmission and reception time shifts are used to control transmission and reception of ultrasonic waves by the probe. The ultrasonic testing condition is such that the respective external refraction angles (or internal refraction angles) of the ultrasonic wave in the plurality of propagation directions are approximately equivalent. The transducers are arranged in a matrix along an annular curved surface designed such that the aforementioned ultrasonic testing condition can be achieved.

In European Patent Publication No. EP 1918700 A1, the phased array is configured as a two-dimensional array, which is expensive and complex to control. At present, one-dimentional dimensional (1D) phased array is being mostly used for industrial applications. For a one dimensional phased array, despite the presence of the electronic steering, it is still necessary to partly perform physical tilting of the probe in order to detect flaws in all orientations. Certainly, being able to quickly and easily tilt the probe is crucial in practice and is addressed in this disclosure.

BRIEF SUMMARY OF THE INVENTION

Ultrasonic nondestructive testing (NDT) methods are commonly used in the inspection of oil country tubular goods. Both manual inspection systems and automated inspection systems have been used for many years. Conventionally, one or more single element ultrasonic probes or multi-element array probes have been used in these systems, and are physically oriented in different directions to detect flaws with different orientations, such as longitudinally oriented flaws, transversely oriented flaws, and obliquely oriented flaws. A given probe can only detect flaws in its specified orientation. Ultrasonic phased array technology has been introduced into the field in recent years. Ultrasonic beams from a phased array probe can be electronically steered to a direction in the azimuth (scanning) plane other than the axial direction of the probe. A single phased array probe still can not detect flaws in all orientations in current inspection systems.

Thus, according to a first aspect of the present invention, an ultrasonic phased array probe apparatus for detecting flaws in a tubular comprises: a probe housing having an axis, a central cavity lying along the axial axis, and a bottom face adapted for placement on the tubular, the bottom face having an opening in the middle; a probe support disposed within the central cavity of the probe housing and rotatable the axial axis of the probe housing which allows the thickness of the wall of the pipe to be measured and flaws to be detected.

In another embodiment, an ultrasonic probe is mounted on the probe support and has a scanning face exposed to the opening of the bottom face of the probe housing, the scanning face being oriented relative to a selected plane of the tubular by rotation of the probe support about the axial axis of the probe housing.

In at least certain embodiments disclosed herein, are systems and methods which employ a single handheld scanner and a single ultrasonic phased array probe to detect wall reduction and longitudinally oriented, transversely oriented, and obliquely oriented flaws in pipes. The phased array probe is mounted on the handheld scanner and the azimuth (scanning) plane of the probe is parallel to the axis of the pipe. The scanner is designed such that the probe can be tilted in the radial plane of the pipe. When the probe is tilted into vertical position, ultrasonic beams can be generated to detect wall reduction if all the active array elements have equal or symmetrical time delay values, or ultrasonic beams can be generated to detect transversely oriented flaws if the elements have unequal time delay values. When the probe is tilted into non vertical positions, ultrasonic beams can be generated to detect either longitudinally oriented flaws if all the active array elements have equal or symmetrical time delay values, or obliquely oriented flaws if the elements have unequal time delay values. The systems and methods disclosed in the present invention can detect obliquely oriented flaws that are in any angle with the axis of the pipe.

In another embodiment, the ultrasonic phased array probe apparatus for detecting flaws in a tubular comprises: a probe housing having a cavity adapted to contain a liquid acoustic couplant and a phased array probe mounted in a back wall of the cavity in the housing; a flexible and conformable acoustic coupling membrane mounted to the probe housing and adapted to contact the tubular and the membrane protrudes from the probe housing to acoustically couple with the tubular and transmit the ultrasound between the phased array probe and the tubular; a fluid regulating device installed to the probe housing allowing the liquid acoustic couplant medium to be injected into and released from the cavity of the probe housing to control the fluid pressure in the cavity; and a beam angle position block conforming to the outside surface of the tubular, and orienting the phased array probe with the tubular.

The tilting of the probe is achived by a beam angle position block that is attached to the bottom of the scanner housing and the beam angle position block rides on the pipe outside surface. The beam angle position block can be quickly and easily attached and detached from the housing. Ultrasound from the phased array probe is coupled into the pipe through direct contact between a membrane on the scanner and the pipe outside surface.

In certain embodiments of the first aspect of the present invention, the bottom face of the probe housing is curved for placement on the tubular.

In certain embodiments of the first aspect of the present invention, the ultrasonic probe is a phased array probe.

In certain embodiments of the first aspect of the present invention, the probe support is provided with a fluid port for delivering fluid to a portion of the central cavity of the probe housing adjacent to the scanning face of the ultrasonic probe.

In certain embodiments of the first aspect of the present invention, the bottom face of the beam angle position block is curved for placement on the tubular.

In certain embodiments of the first aspect of the present invention, the cavity between the phased array probe and the membrane is filled with liquid acoustic couplant.

In certain embodiments of the first aspect of the present invention, the membrane has an acoustic impedance substantially similar to the acoustic impedance of the liquid acoustic couplant medium and seals the acoustic couplant within the cavity, to allow an ultrasonic coupling between the ultrasonic probe and a surface of the tubular.

In certain embodiments of the first aspect of the present invention, the beam angle position block may be detached from the housing.

In another aspect of the present invention, an ultrasonic probe system for detecting flaws in a tubular comprises: a probe housing having an axis, a central cavity lying along the axial axis, and a bottom face adapted for placement on the tubular, the bottom face having an opening in the middle; a probe support disposed within the central cavity of the probe housing and rotatable about the axial axis of the probe housing; an ultrasonic probe mounted on the probe support and having a face exposed to the opening of the bottom face of the probe housing, the scanning face being oriented relative to a selected plane of the tubular to provide a measurement of the thickness of the wall of the pipe and detect flaws in that location, the ultrasonic probe having probe elements configured to generate and receive ultrasonic beams; and a phased array controller for selectively applying varying time delays to probe elements in the ultrasonic probe such that the ultrasonic beams generated by the ultrasonic probe are steered into a direction in or off the normal direction of the ultrasonic probe.

In certain embodiments of the second aspect of the invention, the bottom face of the probe housing is curved for placement on the tubular.

In certain embodiments of the second aspect of the present invention, the ultrasonic probe system further comprises a lock arrangement for selectively preventing rotation of the probe support about the axial axis of the probe housing.

In certain embodiments of the second aspect of the present invention, the probe support is provided with a fluid port for delivering fluid to a portion of the central cavity of the probe housing adjacent to the scanning face of the ultrasonic probe.

In certain embodiments of the second aspect of the present invention, the ultrasonic probe system further comprises an actuator coupled to the probe support for selectively rotating the probe support about the axial axis of the probe housing.

In certain embodiments of the second aspect of the present invention, the ultrasonic probe system further comprises a system controller that issues command signals to the actuator, the actuator being configured to rotate the probe support in response to the command signals.

In certain embodiments of the second aspect of the present invention, the system controller and the phased array controller cooperate to achieve selective steering of the ultrasonic beams generated by the ultrasonic probe and selective tilting of the scanning face of the ultrasonic probe.

In a third aspect of the present invention, a method of testing a tubular for flaws comprises: mounting an ultrasonic probe on a probe support rotatably supported within a central cavity of a probe housing; placing the probe housing on the tubular, with a scanning face of the ultrasonic probe exposed to the tubular through an opening in a bottom of the probe housing; generating and receiving ultrasonic beams using the ultrasonic probe; selectively tilting the scanning face of the ultrasonic probe by rotating the probe support so that the ultrasonic beams generated by the ultrasonic probe are at an angle with an axial plane of the tubular; selectively electronically steering the ultrasonic beams generated by the ultrasonic probe so that the ultrasonic beams generated by the ultrasonic probe are at another angle with a radial plane of the tubular; and processing and interpreting the ultrasonic beams received by the ultrasonic probe to determine if there are flaws in the tubular.

Other aspects and advantages of the invention will be apparent from the following description and the appended claims.

BRIEF DESCRIPTION OF THE DRAWINGS

The accompanying drawings, described below, illustrate typical embodiments of the invention and are not to be considered limiting of the scope of the invention, for the invention may admit to other equally effective embodiments. The figures are not necessarily to scale, and certain features and certain views of the figures may be shown exaggerated in scale or in schematic in the interest of clarity and conciseness.

DETAILED DESCRIPTION OF THE INVENTION

Figure 1:
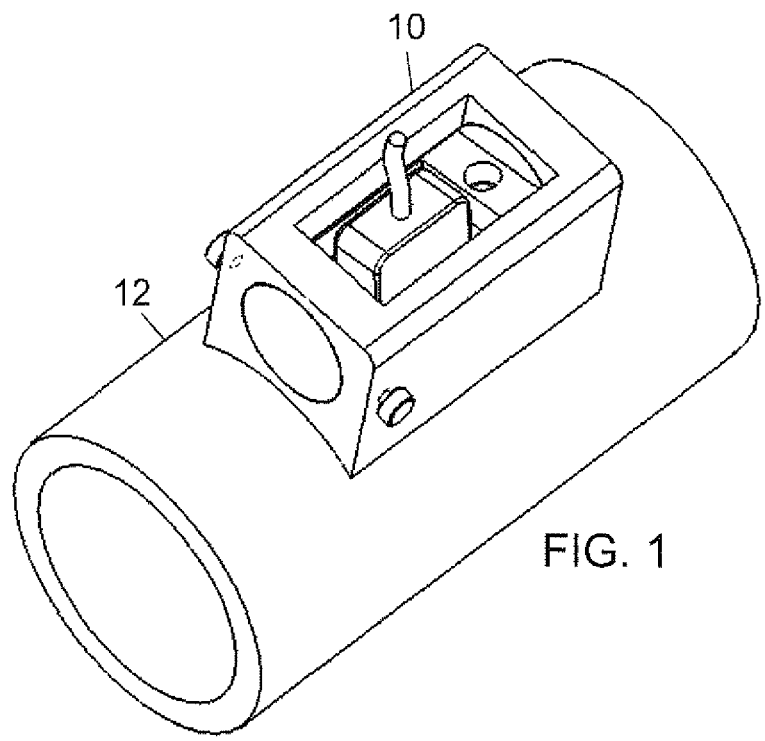
FIG. 1 is a perspective view of an ultrasonic testing system including an ultrasonic probe apparatus sitting on a tubular.

The present invention will now be described in detail, with reference to the accompanying drawings. In this detailed description, numerous specific details may be set forth in order to provide a thorough understanding of the invention. However, it will be apparent to one skilled in the art when the invention may be practiced without some or all of these specific details. In other instances, well-known features and/or process steps may not be described in detail so as not to unnecessarily obscure the invention. In addition, similar reference numerals may be used to identify common or similar elements.

The present invention relates to an ultrasonic testing system capable of flexibly orienting a one-dimensional (but not limited to a one-dimensional) phased array probe in order to detect flaws in any desired direction, (i.e. transverse, longitudinal, or oblique) relative to the axial axis of a tubular.

FIG. 1 shows an ultrasonic testing system including an ultrasonic probe apparatus 10 placed on a tubular 12 for the purpose of detecting structural or material flaws in the tubular 12. Examples of structural and material flaws that may be detected include, without limitation, cracks in the wall of the tubular 12, unevenness in thickness of the wall of the tubular 12, and delaminations and inclusions inside the wall of the tubular 12. The tubular 12 may be, for example, an oilfield tubular, e.g., a drill pipe, or other type of industrial tubular. The tubular 12 may be made of various kinds of materials, for example, metal, plastic, fiber glass, or glass. Typically, the tubular 12 is rigid or semi-rigid.

Figure 2:
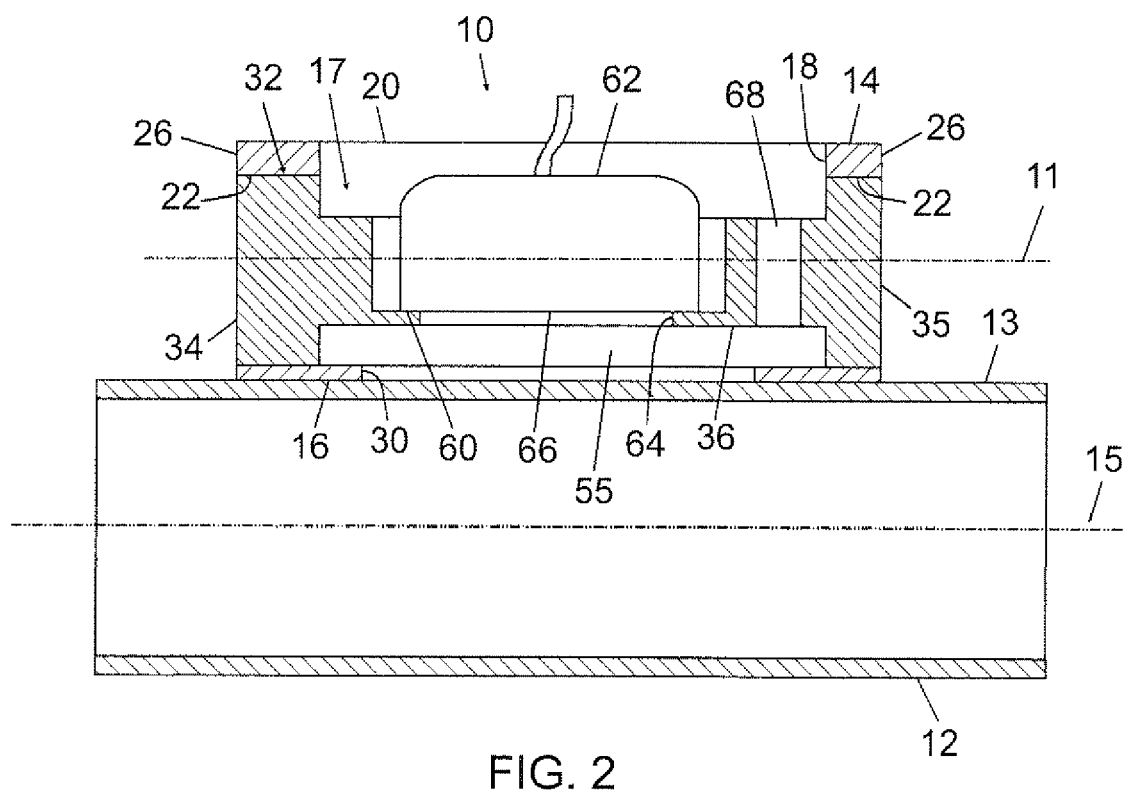
FIG. 2 is a vertical cross-section of the ultrasonic testing system of FIG. 1 along an axial plane of the system.

FIG. 2 is a vertical cross-section of the ultrasonic testing system of FIG. 1. In FIG. 2, the probe apparatus 10 includes a probe housing 14 placed on the tubular 12 such that the axial axis 11 of the probe housing 14 is parallel to the axial axis 15 of the tubular 12. The probe housing 14 has a central cavity 17, which lies along the axial axis 11 of the probe housing 14.

The probe housing 14 has a bottom face 16, top face 20, end faces 26, and side faces (not shown), which together define the boundary of the central cavity 17. The bottom face 16 is adapted for matching the external surface 13 of the tubular 12, as shown in FIG. 2. "Adapted for matching" means, for example, that the face profile of the bottom face 16 is similar to that of the portion of the external surface 13 of the tubular 12 which the bottom face 16 touches. For a tubular 12 having an external surface 13 that is curved, the bottom face 16 would also be curved (see 16 in FIG. 5).

Typically, the surface profile of the bottom face 16 is such that the probe housing 14 can sit on the tubular 12 with little or no gap between the bottom face 16 and the external surface 13 of the tubular 12. An opening 30 is provided in the middle of the bottom face 16. An opening 18 is provided on the top face 20. Openings 22 are provided on the end surfaces 26. The openings 18, 22, and 30 are connected to the central cavity 17 of the probe housing 14.

The probe apparatus 10 includes a probe support 32 inserted in the central cavity 17 of the probe housing 14, with portions disposed in the openings 22 on the end faces 26 of the probe housing 14. The probe support 32 is a rotatable assembly. As an example, the probe support 32 may be composed of wheels 34, 35 disposed within the openings 22 and a support bar 36. The wheels 34, 35 are rotatable about the axial axis 11 of the probe housing 14. The wheels 34, 35 are rigidly connected by a support bar 36 so that when the wheels 34, 35 rotate about the axial axis 11 of the probe housing 14 the support bar 36 also rotates about the axial axis 11. Or the probe support 32 can be a single piece made from a cylinder which can rotate about the axial axis 11. For convenience, it is assumed that the probe support 32 is made of wheels 34, 35 and support bar 36, but this should not be construed as limiting the design of the probe support 32 to one that includes wheels and a support bar. Although not shown, rotary seals may be disposed in the openings 22 to seal between the probe housing 14 and the wheels 34, 35. One reason for providing rotary seals may be to prevent fluid in the central cavity 17, when there is fluid in the central cavity 17, from leaking out of the probe housing 14 through the openings 22. Sound coupling fluid may be supplied into the central cavity 17, as will be explained in more detail below.

Figure 3:
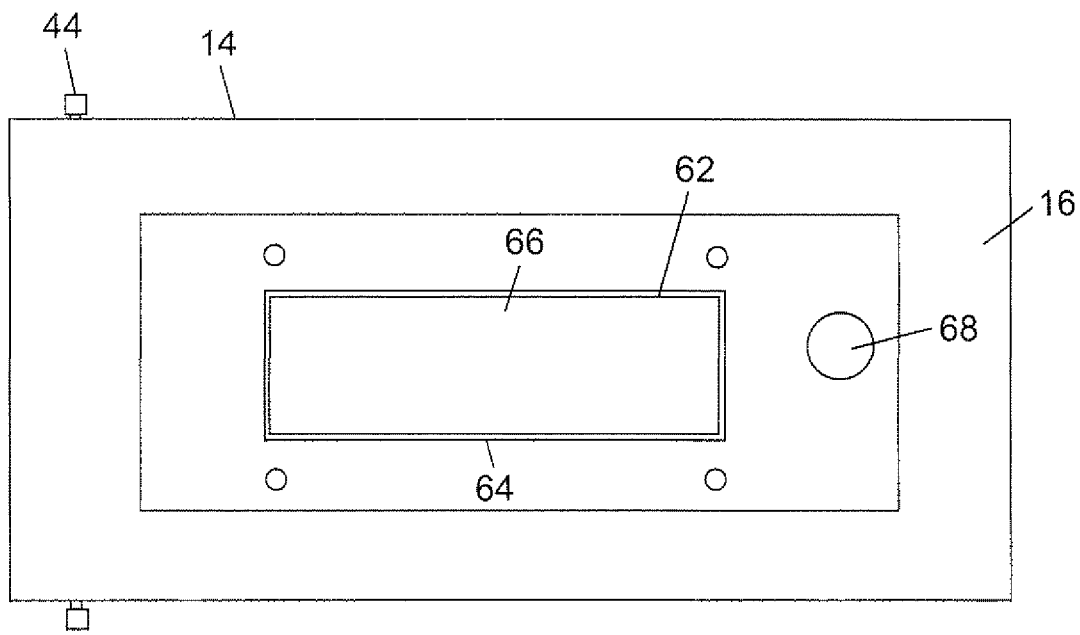
FIG. 3 is a bottom view of the ultrasonic probe apparatus of FIG. 2.

The probe apparatus 10 includes an ultrasonic probe 62 for detecting structural and material flaws in the tubular 12. As shown in FIG. 2, the support bar 36 provides a mounting surface 60 for the ultrasonic probe 62. The mounting surface 60 includes a window 64 through which the scanning face 66 (see also FIG. 3) of the ultrasonic probe 62 is exposed to the central cavity 17 and then the opening 30 in the bottom face 16 of the probe housing 14. With this arrangement, the scanning face 66 of the ultrasonic probe 62 faces the portion of the tubular 12 to be investigated for flaws. The support bar 36, through its rotation about the axial axis 11 of the probe housing 14 as described above, allows the tilt angle of the scanning face 66 and therefore the azimuth plane of the ultrasonic probe 62 to be adjustable relative to the axial axis 15 (or an axial plane passing through the axial axis 15) of the tubular 12. The azimuth plane of the ultrasonic probe 62 is the plane that is perpendicular to the scanning face 66 and crosses the center points of all probe elements in the ultrasonic probe 62. The support bar 36 includes a fluid port 68 for delivering fluid into the space 55 (a portion of the central cavity 17 between the support bar 36 and the bottom face 16 of the probe housing 14 or a portion of the central cavity 17 adjacent to the scanning face 66 of the ultrasonic probe 62). During flaw detection, sound coupling fluid is supplied to the space 55 to provide sound coupling between the ultrasonic probe 62 and the tubular 12. Typically, the sound coupling fluid is water, but other fluids, such as oil, may also be used.

Figure 5:
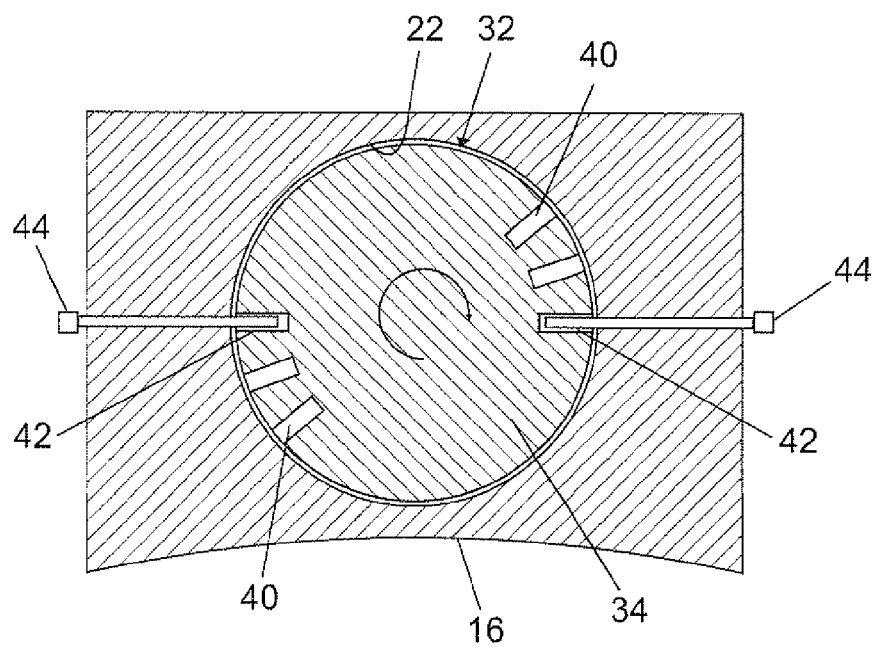
FIG. 5 is a vertical cross-section of an end portion of the ultrasonic probe apparatus of FIG. 2 showing an alternate lock arrangement for a probe support of the ultrasonic probe apparatus.

In one embodiment, the probe apparatus 10 may include a lock arrangement for preventing rotation of the probe support 32 when the support bar 36 is at a selected position corresponding to a selected tilt angle of the scanning face 66 of the ultrasonic probe 62. In one example, and with reference to FIG. 5, the lock arrangement includes radial holes 40 formed at predetermined intervals on wheel 34 (of the probe support). As many holes 40 as desired, with any desired radial spacing between them, may be formed on the wheel 34. Typically, the radial span of the radial holes 40 would be determined by the desired range of tilt angles for the flaw detection. In the example of FIG. 5, the radial holes 40 are formed in the wheel 34 in diametrically-opposed pairs and are accessible from the exterior of the wheel 34. In the example of FIG. 5, the lock arrangement also includes diametrically-opposed holes 42 drilled in the probe housing 14. The holes 42 extend from the exterior of the probe housing 14 to the opening 22 of the probe housing 14 where the wheel 34 is mounted. To rotate the support bar (36 in FIG. 2) to a selected tilt angle, the wheel 34 is rotated such that a selected pair of diametrically-opposed radial holes 40 (corresponding to the selected tilt angle) are aligned with the holes 42 in the probe housing 14. Then, locks 44, e.g., retractable plungers or screws, are inserted into the aligned holes 40, 42 to lock the wheel 34 to the probe housing 14.

Figure 4:
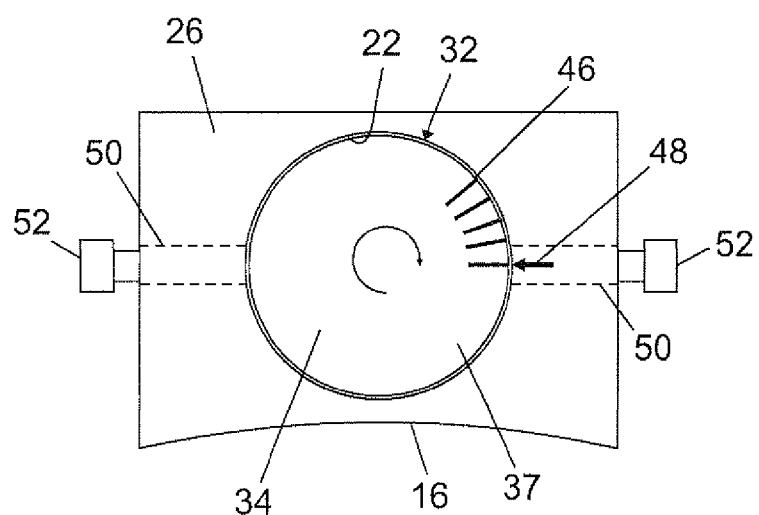
FIG. 4 is an end-view of the ultrasonic probe apparatus of FIG. 2 showing a lock arrangement for a probe support of the ultrasonic probe apparatus.

Another example of a lock arrangement for preventing rotation of the probe support (32 in FIG. 2) when the support bar (36 in FIG. 2) is at a desired position is shown in FIG. 4. In this example, radial marks 46 are formed at predetermined radial positions on the face 37 of the wheel 34 (of the probe support). A pointer mark 48 is formed on the end face 26 of the probe housing 14 where the wheel 34 is mounted. Holes 50 are also formed in the probe housing 14. The holes 50 are through-holes that extend from the exterior of the probe housing 14 to the opening 22 of the probe housing 14 where the wheel 34 is mounted. To rotate the support bar (36 in FIG. 2) to a selected tilt angle, the wheel 34 is rotated such that a selected radial mark 46 (corresponding to the selected tilt angle) is aligned with the pointer mark 48. Then, locks 52, e.g., retractable plungers or screws, are inserted in the holes 50 to hold the wheel 34 at the selected position by pressure.

Figure 6:
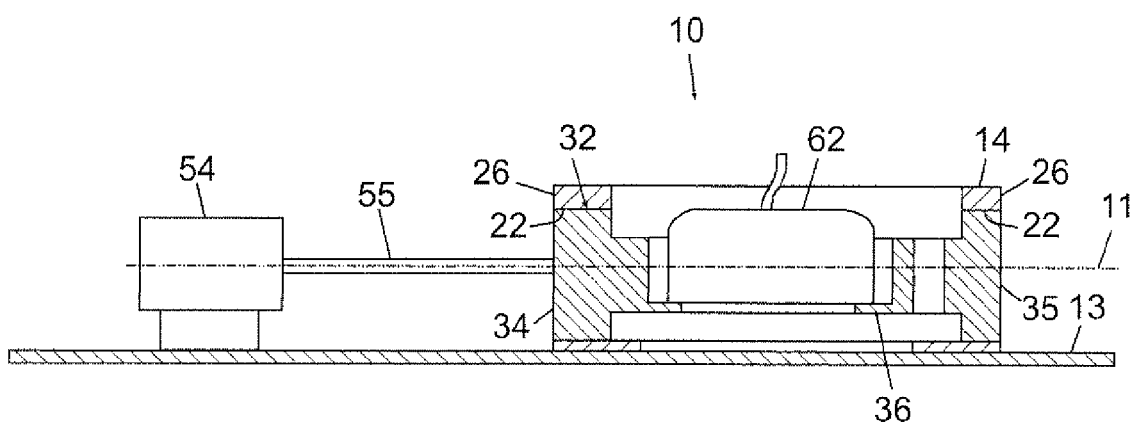
FIG. 6 illustrates an alternate lock arrangement for a probe support of the ultrasonic probe apparatus of FIG. 2.

FIG. 6 shows another example of a lock arrangement for preventing rotation of the probe support 32 when the support bar 36 is at a desired position. In contrast to the previous examples, this lock arrangement may be operated automatically. In the example of FIG. 6, an actuator 54 is coupled to the wheel 34, e.g., via a shaft 55. The actuator 54 is operable to incrementally rotate the shaft 55, and hence rotate the wheel 34 about the axial axis 11 of the probe housing 14. The actuator 54 is equipped to hold the shaft 55 at a desired rotational position, which would also hold the wheel 34 fixed relative to the probe housing 14 and maintain the support bar 36 at the desired tilt angle. The actuator 54 may be, for example, a gear-type indexed shifter or other actuator capable of imparting rotary motion to the wheel 34, on-demand, at desired rotational angle increments. For automatic operation, the actuator 54 may receive command signals from an external source and rotate the probe support 32 (including support bar 36) according to the command signals, thereby allowing automatic shifting of the tilt angle of the ultrasonic probe 62 via rotation of the probe support 32 and subsequent locking of the probe support 32 when the ultrasonic probe 62 is at the desired tilt angle.

Figure 7:
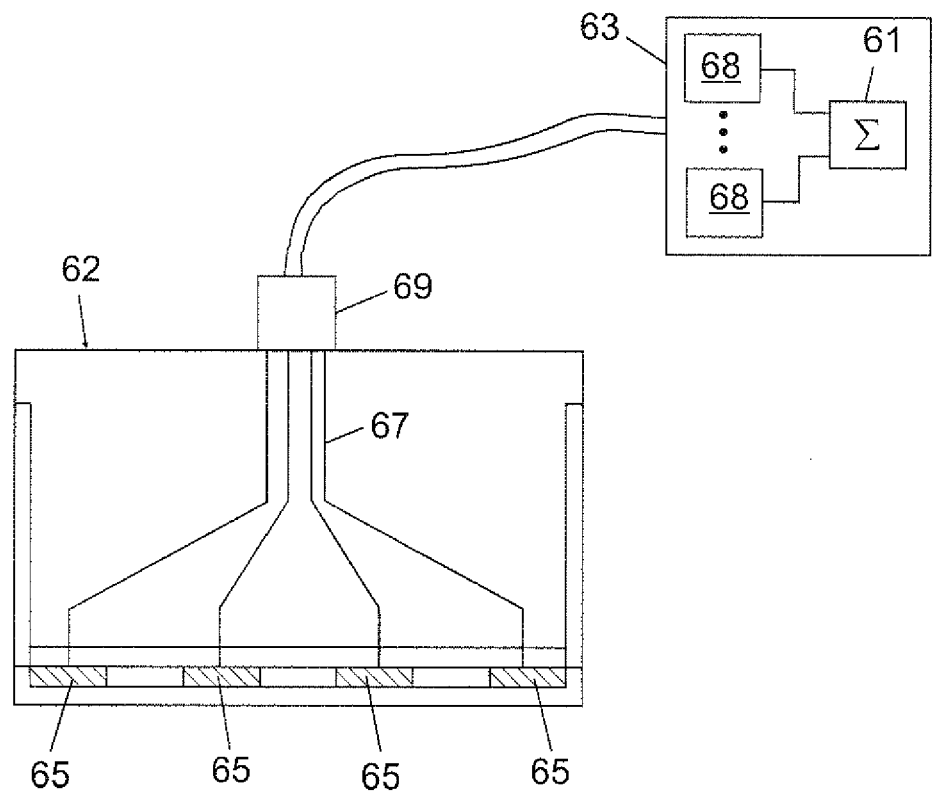
FIG. 7 is a diagram of a phased array probe.
Figure 8:
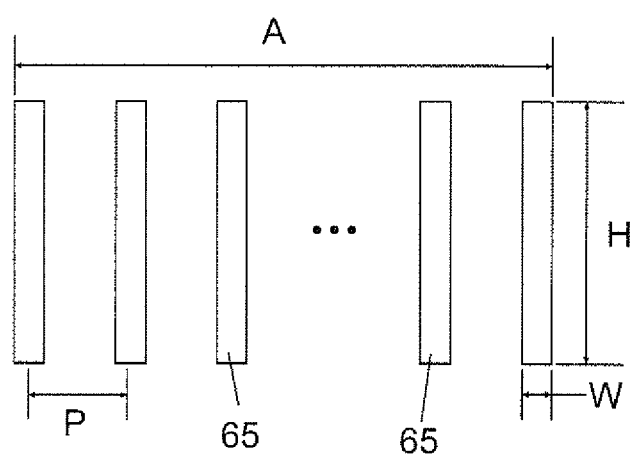
FIG. 8 is a diagram of an array of probe elements for use in a phased array probe.

Returning to FIG. 2, the ultrasonic probe 62 may be a phased array probe. "A phased array probe" is a multi-element ultrasonic transducer that can be used to generate steered beams by means of phased pulsing and receiving. Phased array probes are available in the market. One example of a phased array probe that may be used as the ultrasonic probe 62 is Immersion Phased Array Probe-Flat, available from the General Electric (GE) phased array probe catalog. FIG. 7 shows a typical structure of a phased array probe 62. The phased array probe 62 includes probe elements 65, which are typically provided in multiples of eight, e.g., 16, 32, or 64, and are made of piezoelectric materials, such as piezoelectric ceramic or piezoelectric composite. In FIG. 8, only a few probe elements 65 are shown to simplify the figure (the view in FIG. 8 is from the top or bottom of the array). The probe elements 65 are coupled by element wiring 67 to a multi-conductor coaxial cable 69. FIG. 7 shows a one-dimensional arrangement of the probe elements 65. The dots indicate that there can be as many probe elements 65 as deemed reasonable in the array. "A" represents the aperture of the probe, "P" represents the pitch or center-to-center distance of the probe, "W" represents the width of each probe element, and "H" represents the height of each probe element. The smallest width of the probe element is typically 0.2 mm, and the largest width of the probe element is typically less than 1 mm. Narrower probe elements have more beam spreading, which influences the steering angle of the beam.

For illustration purposes, a phased array probe may have the following parameters: W=0.3 mm, H=10 mm, P=0.8 mm, and 64 probe elements. However, this is just an example of a phased array configuration and in no way imposes any limits on the ultrasonic probe 62, which may employ other equally effective phased array configurations. It should be noted that phased array configurations are not limited to the one-dimensional arrangement shown in FIG. 8. Other arrangements may include two-dimensional square (where the probe elements are arranged as a square matrix), 1.5-dimensional square (where the probe elements are arranged as a square matrix, but with different lengths of probe elements), one-dimensional annular (where the probe elements are circular and concentric), two-dimensional segmented annular (where the probe elements are arranged in segments along concentric, annular paths), and one-dimensional circular (where the probe elements are oriented radially).

Returning to FIG. 7, the coaxial cable 69 leads to a phased array controller 63 containing phased array control circuits 68. The control circuits 68 are customized to have a limited number of pulse channels (typically only a fraction of the total element number in order to reduce cost) and a certain amount of switches to control which elements among them are triggered by the pulses each time. Explicitly, the phased array control circuits 68 select a group of probe elements 65 and use the selected group to generate ultrasound by sending a high voltage pulse to each of the probe elements 65 in the selected group. The probe elements 65 in the selected group thus contribute to the active aperture, i.e., active probe length. The probe elements 65 convert electrical energy to mechanical energy in the form of ultrasonic waves, which are transmitted to the tubular under test. The high voltage pulses can be sent at the same time or at different times, i.e., with different time delays. If the latter, the ultrasonic beam could be steered to a direction other than the normal direction of the probe. After ultrasound generation, the phased array control circuits 68 can select the same group or a different group of probe elements to receive ultrasonic waves coming back from the tubular under test. The probe elements 65 receiving the ultrasonic waves would convert the ultrasonic waves into electric signals, which would then be received by the phased array control circuits 68 and processed. The electrical signals can be delayed differently and then summed in the phased array controller 63, as shown at 61. Time delay processing in both the ultrasound generation and receiving is referred to as electronic steering.

Figure 9:
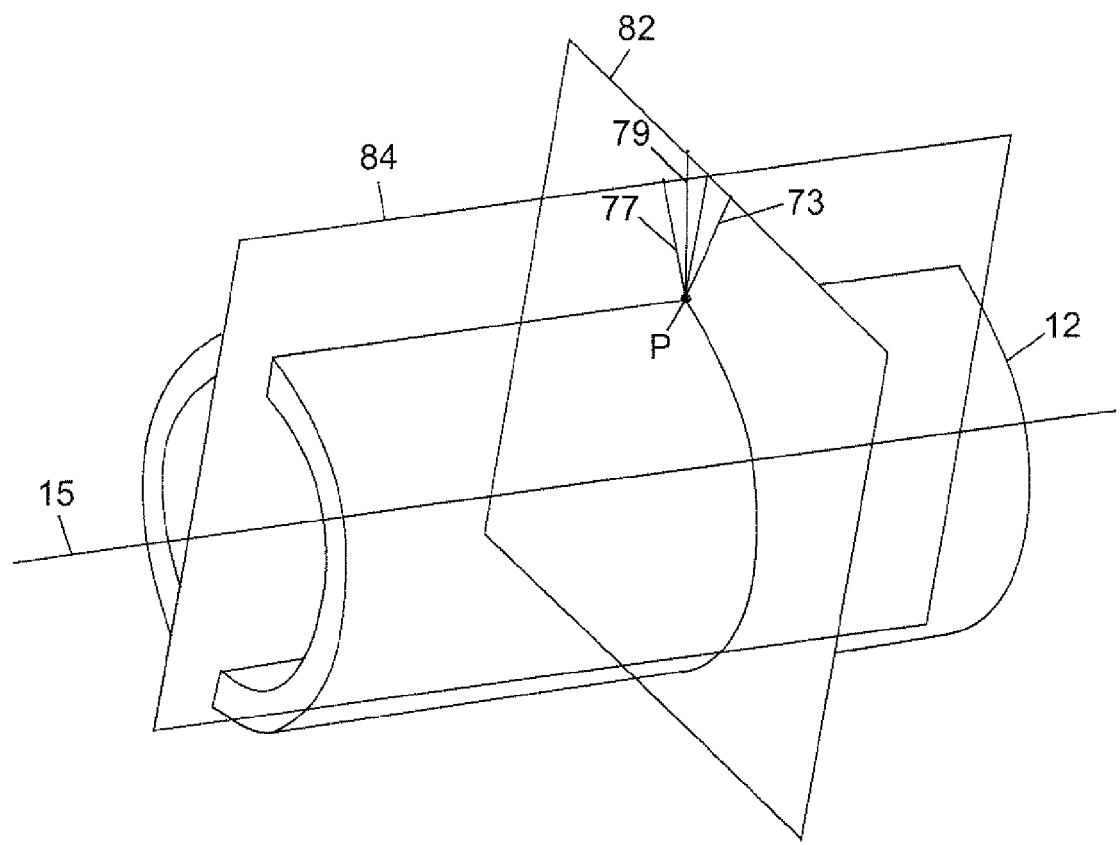
FIG. 9 shows axial and radial planes of a tubular, and ultrasonic beam directions for detecting flaws in different orientations.

FIG. 9 shows the tubular 12 with a radial plane 82 and an axial plane 84. The axial plane 84 is along the axial axis 15 of the tubular 12, while the radial plane 82 is perpendicular to the axial plane 84. Initially, the ultrasonic probe (62 in FIG. 2) is oriented such that the azimuth plane of the ultrasonic probe 62 coincides with the axial plane 84 of the tubular 12 and the elevation plane (perpendicular to the azimuth plane) of the ultrasonic probe 62 coincides with the radial plane 82 of the tubular 12. To detect flaws in all orientations, the probe system must have the ability to generate ultrasonic beams that are either in both the radial plane 82 and axial plane 84, or at an angle with one or both of the radial plane 82 and axial plane 84. This is demonstrated with reference to FIGS. 9-11.

Figure 10:
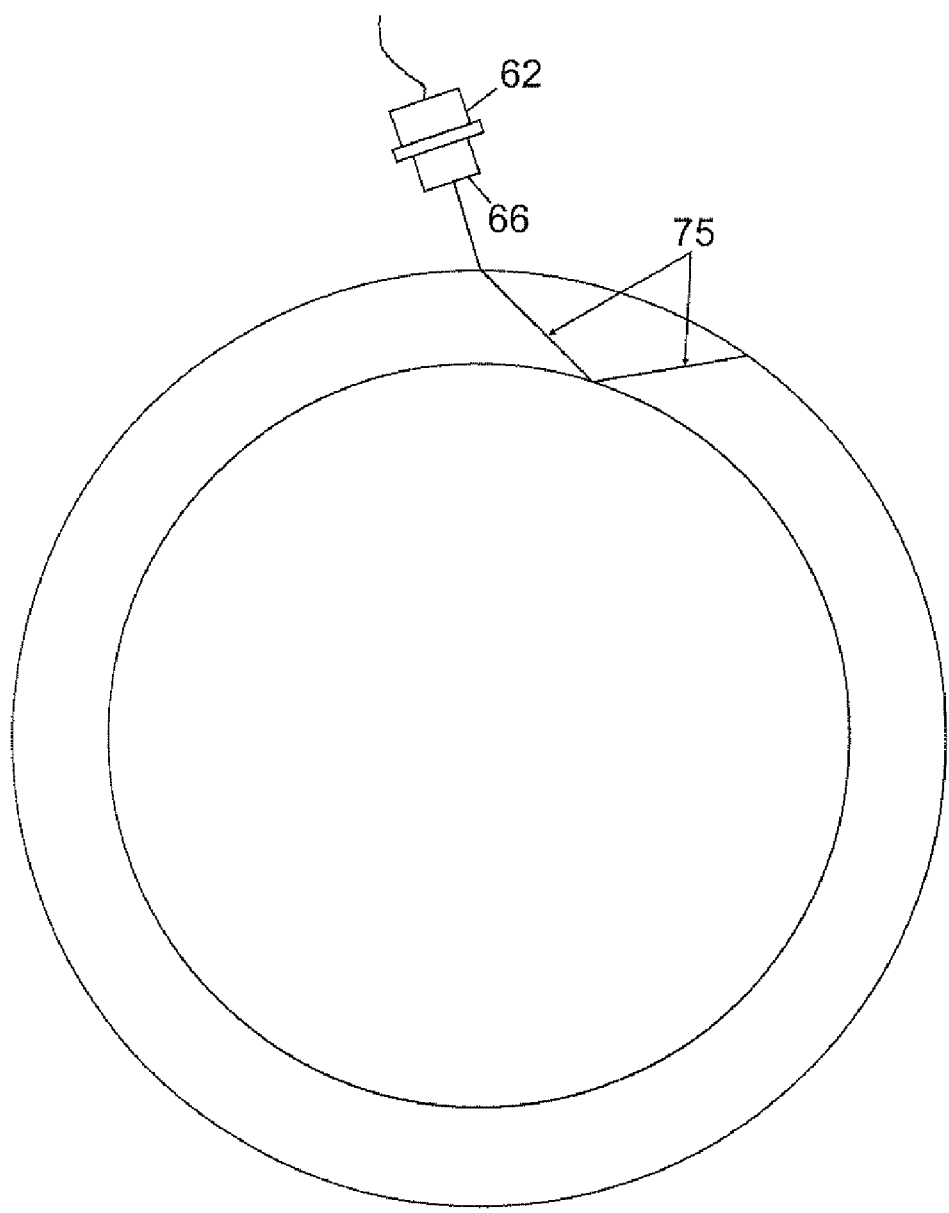
FIG. 10 shows ultrasonic beams in a tubular for detecting longitudinally-oriented flaws.

Referring to FIG. 9, to detect a longitudinally-oriented flaw, i.e., a flaw parallel to the axial axis 15 of the tubular 12, ultrasonic beams generated by the ultrasonic probe have to reside in the radial plane 82 of the tubular 12 that contains the incident point "P", but at an angle, typically between 13° and 20°, with the axial plane 84 of the tubular 12 that contains the point "P". The ultrasonic beam direction for detecting a longitudinally-oriented flaw is indicated at 73. FIG. 10 shows a cross-section of the tubular 12, along the radial plane 82, with ultrasonic beams 75 in the tubular 12 for detecting longitudinally-oriented flaws.

Figure 11:
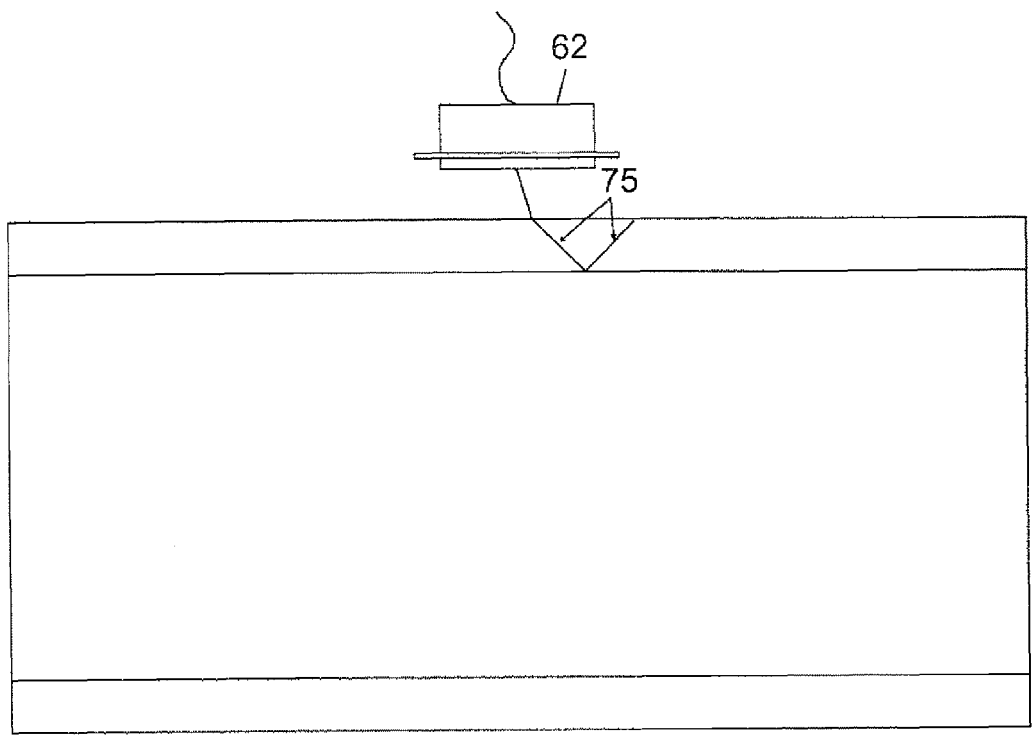
FIG. 11 shows ultrasonic beams in a tubular for detecting transversely-oriented flaws.

Returning to FIG. 9, to detect a transversely-oriented flaw, i.e., a flaw that is perpendicular to the axial axis 15 of the tubular 12, ultrasonic beams generated by the ultrasonic probe have to reside in the axial plane 84 of the tubular 12 that contains the incident point "P", but at an angle, typically between 13° and 20°, with the radial plane 82 of the tubular 12 that contains the point "P". The ultrasonic beam direction for detecting a transversely-oriented flaw is indicated at 77. FIG. 11 shows a cross-section of the tubular 12, along the axial plane 84, with ultrasonic beams 75 in the tubular 12 for detecting transversely-oriented flaws.

Returning to FIG. 9, to detect an obliquely-oriented flaw, i.e., a flaw that is neither parallel to nor perpendicular to the axial axis of the tubular article, ultrasonic beams generated by the probe 62 are neither in the axial plane 84 nor in the radial plane 82 of the tubular 12 that contains the incident point "P", but at an angle, typically between 0° and 20°, with both the axial plane 84 and the radial plane 82. An ultrasonic beam direction for detecting an obliquely-oriented flaw is indicated at 79.

Figure 12:
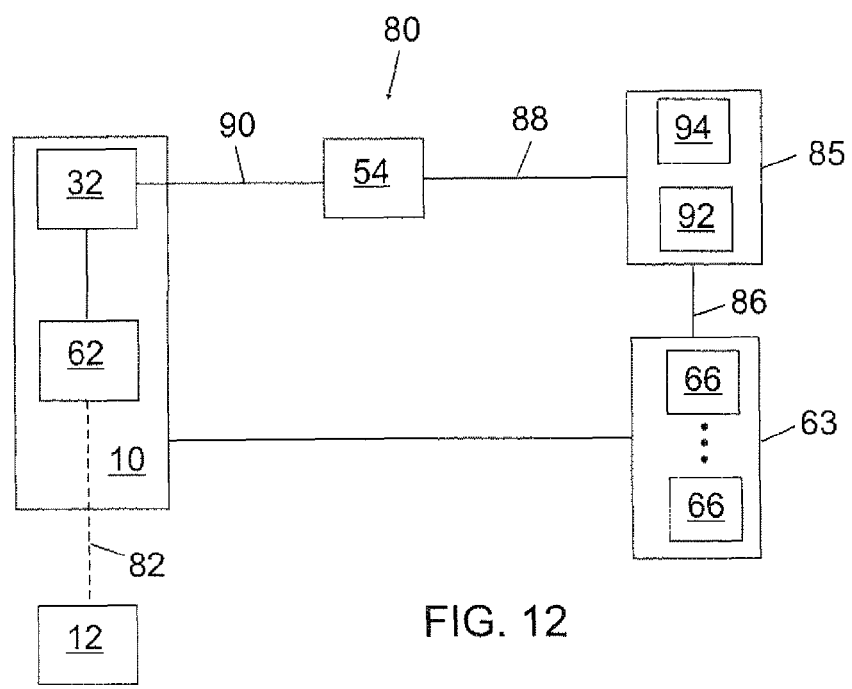
FIG. 12 illustrates an ultrasonic probe system including the ultrasonic probe apparatus of FIG. 2.
Figure 13:
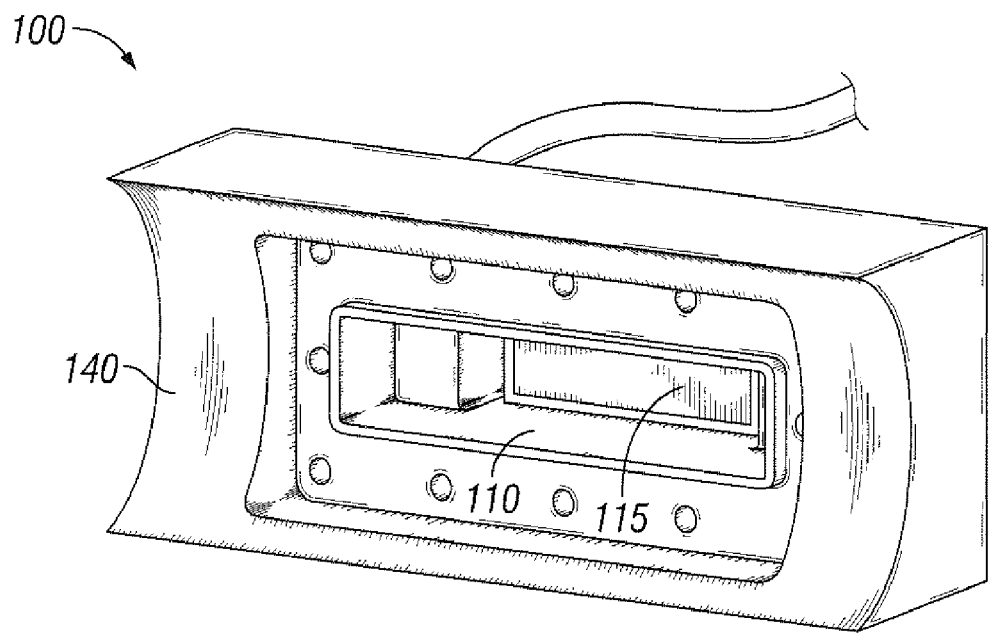
FIG. 13 illustrates another embodiment of the ultrasonic probe system of the present invention, wherein the membrane has been disassembled to expose cavity and the face of the phased array probe.

FIG. 12 shows a block diagram of a probe system 80 including the probe apparatus 10 described above and tubular 12. The probe support 32 and ultrasonic probe 62 of the probe apparatus 10 are shown. The line 82 between the probe apparatus 10 and the tubular 12 indicates that the probe apparatus 10 is placed on the tubular 12, as shown in FIG. 2, or otherwise arranged such that the ultrasonic probe 62 can transmit ultrasonic waves to and receive ultrasonic waves from the tubular 12. The probe system 80 includes a phased array controller 63, which is connected to the ultrasonic probe 62. The phased array controller 63 selectively applies varying time delays to the probe elements in the ultrasonic probe 62 so that ultrasonic beams generated by the ultrasonic probe can be steered into a direction in or off the normal direction of the probe. The probe system 80 includes a system controller 85, which can communicate with the phased array controller 63, as indicated at 86. The probe system 80 may include an actuator 54, as previously explained, for rotating a wheel of the probe support (or for rotating the probe support 32) and locking the wheel (or locking the probe support 32) in place. In this case, the system controller 85 may communicate with the actuator 54, as indicated at 88. Line 90 represents a rotatable link between the actuator 54 and the probe support 32 of the probe apparatus 10.

The system controller 85 includes a processor 92 and may include other supporting devices, generally indicated at 94, such as a memory device and a display device. In one example, the processor 92 computes a desired tilt angle for the ultrasonic probe 62 to detect a particular flaw in a particular orientation in the tubular 12. The system controller 85 may display the tilt angle information on a display device so that a user can read the information and then use the information to rotate the probe support 32 to position the ultrasonic probe 62 at the desired tilt angle. Alternately, the system controller 85 may send a command signal to the actuator 54 to rotate the probe support 32 to position the ultrasonic probe 62 at the desired tilt angle. The processor 92 may also compute information that can be used to automatically and electronically steer the probe elements of the ultrasonic probe 62. In this case, the system controller 85 and the phased array controller 63 would work together to achieve the desired electronic steering of the ultrasonic beams.

The probe system 80 described above is equipped to generate ultrasonic beams and receive ultrasonic beams in varying directions and angles. The received ultrasonic beams are processed and interpreted to determine if flaws are present in the tubular. The processing and interpreting may be achieved using the processor 92 or by manual calculations. By monitoring the signals returning from the tubular wall one usually chooses a few time intervals where only low noise would appear for a flawless tubular. If the actually received signals within these intervals are larger than a specified level, they are interpreted to be caused by flaws. As described above, the probe support 32 can be rotated to tilt the scanning face (66 in FIGS. 2 and 3) of the ultrasonic probe 62 so that the ultrasonic beams it emits are at an angle with the axial plane of the tubular 12.

Furthermore, in the azimuth plane of the probe, ultrasonic beams can be electronically steered into a direction other than the normal direction of the probe by applying varying time delays to individual probe elements within an active aperture of the phased array so that beams can also be at an angle with the radial plane. These two angles (the one achievable by rotation of the probe support and the one achievable by electronic steering) can be adjusted independently, e.g., between 0° and 20°. To detect flaws in any given orientation, as described above, the two required angles are calculated, either manually or using the processor. The probe support is then rotated to obtain the required beam angle with the axial plane, and proper time delays are applied to the probe elements to obtain the required beam angle with the radial plane. For example, simple linear time delays (i.e., a constant time interval between two adjacent delays) can be used to electronically tilt the beam at the proper angle relative to the radial plane.

Figure 15:
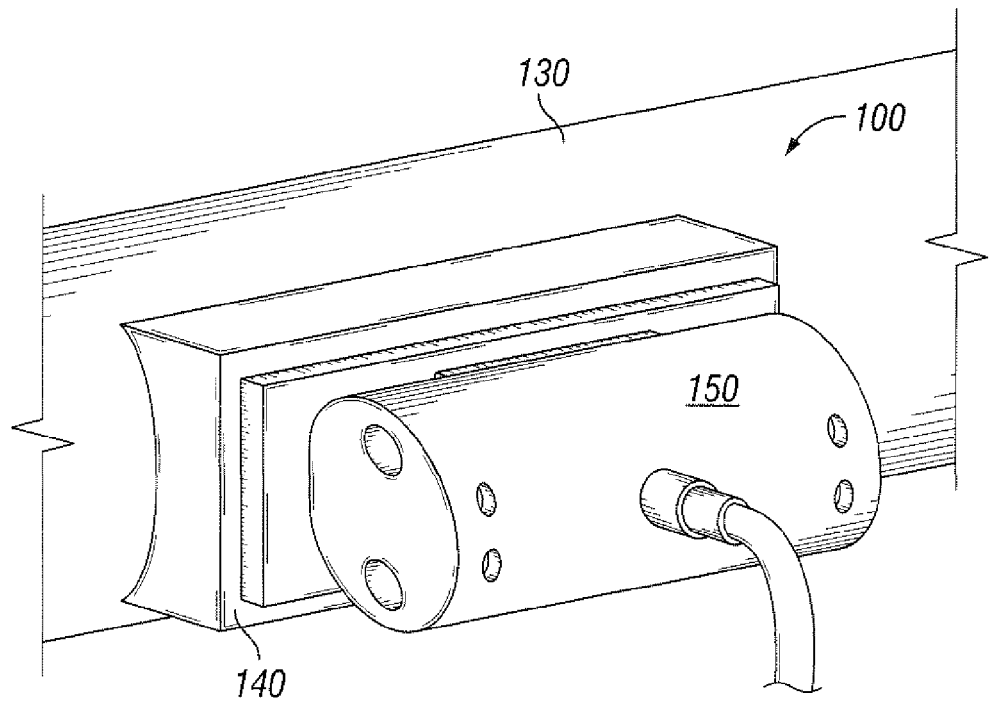
FIG. 15 illustrates one embodiment of the ultrasonic probe apparatus of the present invention as it would be used to measure wall thickness and determine if there are transversely oriented flaws in a pipe being tested.
Figure 16:
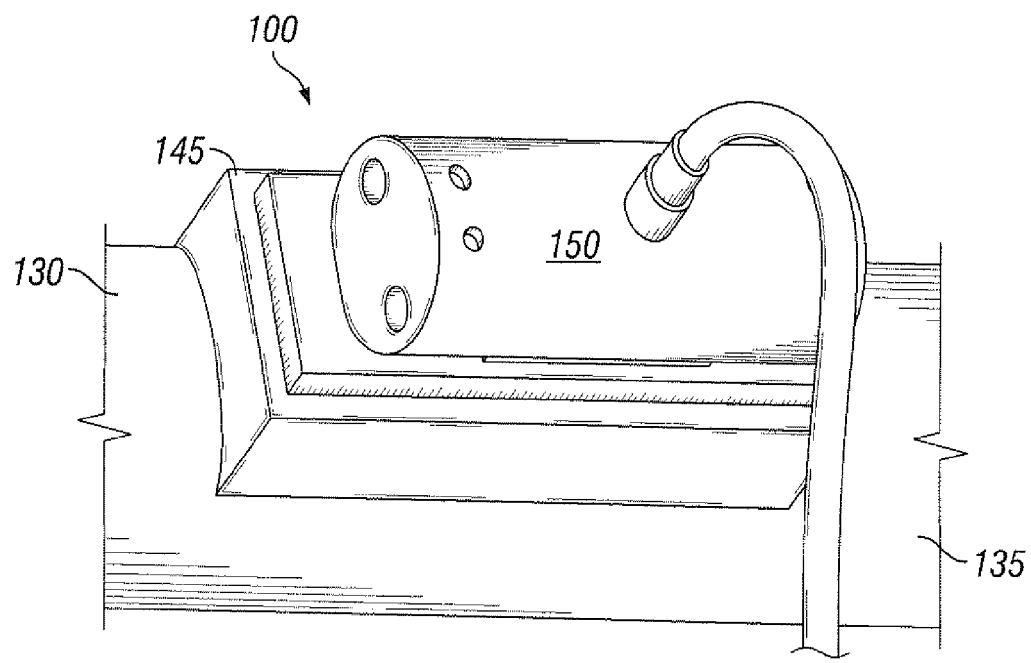
FIG. 16 illustrates another embodiment of the ultrasonic probe apparatus of the present invention as it would be used to determine if there has been longitudinally and obliquely oriented flaws in a pipe being tested.
Figure 17:
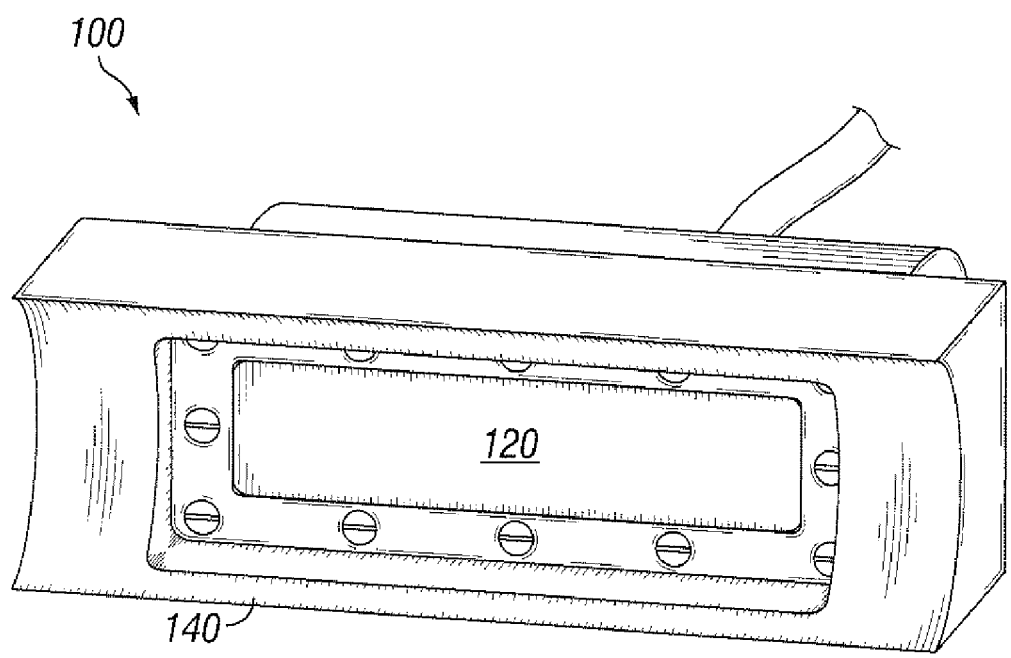
FIG. 17 is a view of a typical membrane used for an ultrasonic probe apparatus of the present invention.

One preferred design of an ultrasonic scanning probe apparatus of the present invention, as illustrated in FIGS. 13-17, is a phased array ultrasonic probe apparatus 100 comprising a cavity 110 filled with water or other suitable ultrasonic wave propagation fluid (not shown), and sealed with an acoustically transparent membrane 120 (FIG. 17). The membrane 120 is intended to contact the outside surface the pipe 130 or other surface being scanned for flaws, and replaces the flowing liquid (typically water, but may be other liquids) as the acoustic couplant. The membrane itself is made of a material that is sonically 'transparent' to the ultrasonic frequencies used by the probe. This arrangement therefore allows essentially 'dry' acoustical testing of the pipe 130 (as long as the pipe surface is dampened by an acoustic coupling fluid), as the acoustic couplant is sealed within the cavity 110 of the probe apparatus 100 by the acoustically transparent membrane 120. This arrangement, therefore, eliminates the need to continuously supply acoustic coupling fluid between the ultrasonic probe and the outside surface of the pipe. In addition to being much easier, and far more convenient to use, this arrangement also allows for ultrasonic testing for flaws in tubulars in areas where it would not be practical to handle the supply and drainage of the large quantities of running acoustic coupling fluid presently applied to pipes as an ultrasonic couplant. This may be especially useful in very cold climates where freezing the water (or other fluid) may be a problem, or in crowded areas where slipping hazards may exist, or in areas where large quantities of clean couplant fluid are difficult to obtain. In addition, the sealed system eliminates measurement variables that may exist in the 'running fluid' systems.

As illustrated in FIG. 17, a bottom view of the probe apparatus is shown generally at 100, showing the membrane 120 in place. The cavity 110 (shown in FIG. 13) between the face of the phased array probe 115 and the membrane 120 may be filled with water or other type ultrasound couplant. In operation, while the beam angle position block 140 rides on the pipe surface 135 (as shown in FIG. 16), the membrane 120 will be in contact with the pipe outside surface 135 so the ultrasound from the phased array probe 115 can be coupled into the pipe body 130 through the fluid in the cavity 110 and the membrane 120, therefore running acoustic coupling fluid is not needed for sound coupling, as is the present practice.

In order to assure good contact between the membrane 120 and the pipe body 130, the membrane 120 may be allowed to protrude slightly from the housing and remain slightly underfilled, so as to remain very flexible. This allows the membrane 120 to deform and therefore conforms to the pipe outside surface when it is brought into contact with the surface. This means that care must be taken to maintain proper fluid pressure inside the cavity 110. Therefore, some control of the fluid volume and pressure inside the cavity 110 is typically necessary. In addition, the fluid pressure which may be maintained inside the cavity 110 may also be used to control the contact pressure between the membrane 120 and the pipe outside surface. This pressure control may be achieved by installing a fluid regulating device, for example, but not limited to, a check valve, through which acoustic coupling fluid can be injected into or released from the cavity 110. There is a small amount of standoff built into the beam angle position block 140 to assure that the membrane 120 does not get pinched by the pipe while being used.

Figure 14:
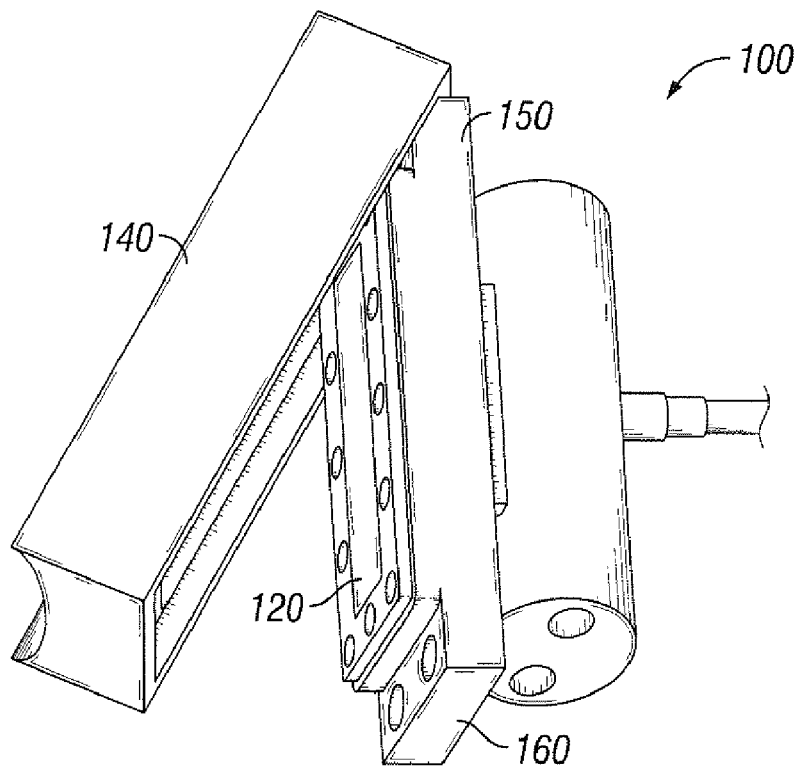
FIG. 14 is a partially assembled view of the ultrasonic probe system of FIG. 13, wherein beam angle position block has been partially detached to show the membrane assembled to the probe housing.

Shown in FIG. 14 is the scanner 150 with the beam angle position block 140 partially detached from the housing 160. The beam angle position block 140 may be removable and modular so that many different configurations of beam angles and pipe diameters are possible by changing just the block 140. These beam angle position blocks 140 may be secured to the housing 160 by magnetic force (or other means) for easy and quick change of beam angle position blocks 140 of differing configurations. The beam angle position blocks 140 may be used to define the angle between the azimuth plane of the phased array probe 115 and the axial plane of the pipe 130, and the two planes intersect at the beam entry point on the pipe 130 outside surface (see FIG. 9 and its descriptions). This angle changes when the probe housing 160 is tilted to a different position in the radial plane of the pipe by using a different beam angle position block 140, as a result, the contact between the membrane 120 and the pipe 130 also changes. Because the membrane 120 is very flexible, it can deform and re-conform to the pipe outside surface. This means the same scanner 150 can be used to detect transversely oriented, longitudinally oriented, and obliquely oriented defects—and to measure wall thickness by simply changing beam angle position block 140. This is a notable improvement over conventional ultrasonic contact testing methods in the existing art where the phased array probe is coupled to a sound coupling block (a solid wedge) and then the solid wedge is coupled to the part under test. In these prior systems, the solid wedge defines the beam angle of the phased array probe and different wedges are required for defects with different orientations. The phased array probe is mounted to the wedge by screws. The ultrasonic probe of the present invention does not need these types of wedges, which markedly improves its utility over the prior art, as it is a very time consuming task to change wedges.

As shown in FIG. 15, the scanner 150 is on a pipe 130 with a beam angle position block 140 that orients the phased array probe such that the azimuth plane of the phased array probe coincides with the axial plane of the pipe and the elevation plane (perpendicular to the azimuth plane) of the phased array probe coincides with the radial plane of the pipe. This arrangement makes ultrasonic beams generated by the phased array probe always reside in the axial plane of the pipe and may measure pipe wall thickness if the ultrasonic beams are perpendicular to the pipe outside surface and detect transversely oriented flaws in the pipe 130 such as cracks and other flaws if the ultrasonic beams are in a angle with the normal of the pipe outside surface.

In FIG. 16 is an embodiment where a scanner 150 may be provided with a tilting beam angle position block 145 attached for detecting longitudinally and obliquely oriented flaws on the pipe 130. In this configuration the block 145 orients the phased array probe such that the azimuth plane of the phased array probe is at a non-zero angle with the axial plane of the pipe and the elevation plane (perpendicular to the azimuth plane) of the phased array probe still coincides with the radial plane of the pipe. As explained in FIG. 9, in this arrangement, ultrasonic beams generated by the phased array probe can be used to detect longitudinally oriented flaws if they reside in the radial plane of the pipe that contains the beam incident point, but at an angle with the axial plane of the pipe that contains the beam incident point. In this arrangement, ultrasonic beams generated by the phased array probe can also be used to detect obliquely oriented flaws if they are neither in the axial plane nor in the radial plane of the pipe that contains the beam incident point, but at an angle with both the axial plane and the radial plane.

With only a minor interruption in the work flow, one beam angle position block 140 may be exchanged for another. Therefore, due to the modular construction of the scanner 150, a collection of many different beam angle position blocks 140 may be readily interchanged for various types of testing.

Also, because this ultrasonic scanning probe system uses a 'closed' coupling media it may furthermore be useful in circumstances where a flowing liquid system of the prior art would not be practical. For example, in incidences where the environment is very cold, a water couplant may be inappropriate due to freezing of the water, wherein in the present invention a small amount of antifreeze may be added to the ultrasound couplant allowing it to work properly. In other instances, a supply of running water to use as a couplant may just not be available. In still other instances, the environment of the testing area may not have the drainage facility to dispose of running water.

Therefore, whereas the present invention has been described in particular relation to the drawings attached hereto, it should be understood that other and further modifications apart from those shown or suggested herein, may be made within the scope and spirit of the present invention. Those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An ultrasonic testing apparatus for detecting flaws in a tubular, comprising:
   a handheld scanner with a single ultrasonic probe mounted therein comprising a probe housing having a cavity adapted to contain a liquid acoustic couplant medium having an acoustic impedance, and a phased array probe mounted in a back wall of the cavity in the probe housing;
   a flexible and conformable acoustic coupler membrane mounted to the probe housing and adapted to contact the tubular and having an acoustic impedance substantially similar to the liquid acoustic impedance of the liquid acoustic couplant medium, the acoustic coupler membrane sealing the liquid acoustic couplant medium within the cavity to allow an ultrasonic coupling between the ultrasonic probe and a surface of the tubular, wherein the membrane protrudes from the probe housing to acoustically couple with the tubular and transmit ultrasound between the phased array probe and the tubular;
   a fluid regulating device installed to the probe housing allowing the liquid acoustic couplant medium to be injected into and released from the cavity of the probe housing to control the fluid pressure in the cavity; and
   a beam angle position block conforming to the surface of the tubular, and orienting the phased array probe with the tubular.

2. The ultrasonic testing apparatus of claim 1 wherein the beam angle position block provides a replaceable wear surface for the ultrasonic probe.

3. The ultrasonic testing apparatus of claim 1, wherein the bottom face of the beam angle position block is curved for placement on the tubular.

4. The ultrasonic testing apparatus of claim 1, wherein the ultrasonic probe is a phased array probe.

5. The ultrasonic testing apparatus of claim 1 wherein the cavity between the phased array probe and the membrane is filled with liquid acoustic couplant.

6. The ultrasonic testing apparatus of claim 1, wherein the beam angle position block may be detached from the housing.

7. The ultrasonic testing apparatus of claim 1, wherein the beam angle position block is secured to the probe by magnetic force for rapid changing of the beam angle position block with different tilting angles.

8. The ultrasonic testing apparatus of claim 1 comprising a non-tilting beam angle position block attached for detecting wall reduction and transversely oriented flaws in the tubular.

9. The ultrasonic testing apparatus of claim 1 comprising a tilting beam angle position block for detecting longitudinally and obliquely oriented flaws in the tubular.

10. An ultrasonic testing apparatus for detecting flaws in a tubular, comprising:
    a probe housing having an axial axis, a central cavity lying along the axial axis, and a bottom face adapted for placement on the tubular, the bottom face having an opening in the middle. the probe housing having a probe cavity adapted to contain a liquid acoustic couplant medium having an acoustic impedance;
    a probe support disposed within the central cavity and rotatable about the axial axis of the probe housing;
    an ultrasonic probe mounted on the probe support and having a scanning face exposed to the opening of the bottom face of the probe housing, the scanning face being oriented relative to a selected plane of the tubular by rotation of the probe support about the axial axis of the probe housing;
    a flexible and conformable acoustic coupler membrane mounted to the probe housing and adapted to contact the tubular and having an acoustic impedance substantially similar to the acoustic impedance of the liquid acoustic couplant medium, the acoustic coupler membrane sealing the liquid acoustic couplant medium within the probe cavity to allow an ultrasonic coupling between the ultrasonic probe and a surface of the tubular, wherein the membrane protrudes from the probe housing to acoustically couple with the tubular and transmit ultrasound between the ultrasonic probe and the tubular; and
    a fluid regulating device installed to the probe housing allowing the liquid acoustic couplant medium to be injected into and released from the central cavity of the probe housing to control the fluid pressure in the central cavity.

11. An ultrasonic probe system for detecting flaws in a tubular, comprising:
    a probe housing having an axial axis, a central cavity lying along the axial axis, and a bottom face adapted for placement on the tubular, the bottom face having an opening in the middle. the probe housing having a probe cavity adapted to contain a liquid acoustic couplant medium having an acoustic impedance;
    a probe support disposed within the central cavity of the probe housing and rotatable about the axial axis of the probe housing;
    an ultrasonic probe mounted on the probe support and having a scanning face exposed to the opening of the bottom face of the probe housing, the scanning face being oriented circumferentially relative to a selected plane of the tubular by rotation of the probe support about the axial axis of the probe housing, and the ultrasonic probe having probe elements configured to generate and receive ultrasonic beams;
    a flexible and conformable acoustic coupler membrane mounted to the probe housing and adapted to contact the tubular and having an acoustic impedance substantially similar to the acoustic impedance of the liquid acoustic couplant medium, the acoustic coupler membrane sealing the liquid acoustic couplant medium within the probe cavity to allow an ultrasonic coupling between the ultrasonic probe and a surface of the tubular. wherein the membrane protrudes from the probe housing to acoustically couple with the tubular and transmit the ultrasound between the ultrasonic probe and the tubular;
    a fluid regulating device installed to the probe housing allowing the liquid acoustic couplant medium to be injected into and released from the central cavity of the probe housing to control the fluid pressure in the central cavity; and
    a phased array controller for selectively applying varying time delays to probe elements in the ultrasonic probe such that the ultrasonic beams generated by the ultrasonic probe are steered into a direction in or off the normal direction of the ultrasonic probe.

12. The system of claim 11, wherein the bottom face of the probe is curved for placement on the tubular.

13. A method of testing a tubular for flaws, comprising:

mounting a probe housing, comprising a beam angle position block conforming to a diameter of the tubular, and orienting a phased array probe with the tubular;

the probe housing having a cavity adapted to contain a liquid acoustic couplant medium having an acoustic impedance, and the phased array probe mounted in a back wall of the cavity in the probe housing, providing a flexible, conformable acoustic coupler diaphragm adapted to contact the tubular having an acoustic impedance substantially the same as an acoustic impedance of the couplant, sealing the liquid acoustic couplant medium within the cavity with the acoustic coupler diaphragm, to allow an ultrasonic coupling between the probe and a surface of the tubular, the membrane protrudes from the probe housing to couple with the tubular and conduct the ultrasound between the phased array probe and the tubular, placing the probe on the tubular with a scanning face of the ultrasonic probe exposed to detect flaws in the tubular through ultrasonic coupling of the acoustic coupler diaphragm.

14. The method of testing a tubular for flaws of claim 13 wherein the ultrasonic probe is a phased array probe.

15. The method of testing a tubular for flaws of claim 13 wherein the cavity between the phased array probe and the membrane is filled with liquid acoustic couplant.

16. The method of testing a tubular for flaws of claim 13, wherein the beam angle position block may be detached from the housing.

17. The method of testing a tubular for flaws of claim 13, wherein the beam angle position block is secured to the probe by magnetic force for rapid changing of the beam angle position block with different tilting angles.

18. The method of testing a tubular for flaws of claim 17 further comprising a non-tilting beam angle position block attached for detecting wall reduction and transversely oriented flaws in the tubular.

19. The method of testing a tubular for flaws of claim 17 further comprising a tilting beam angle position block for detecting longitudinally and obliquely oriented flaws in the tubular.

* * * * *